(12) United States Patent
Villahermosa

(10) Patent No.: US 8,622,944 B1
(45) Date of Patent: Jan. 7, 2014

(54) MODULAR ARTICULATING SPLINT

(76) Inventor: Alexander Jesus Villahermosa, Woodbridge, VA (US)

( * ) Notice: Subject to any disclaimer, the term of this patent is extended or adjusted under 35 U.S.C. 154(b) by 0 days.

(21) Appl. No.: 13/543,793

(22) Filed: Jul. 7, 2012

(51) Int. Cl.
*A61F 5/00* (2006.01)

(52) U.S. Cl.
USPC .................. 602/5; 602/20; 602/23; 128/870; 128/878; 128/882

(58) Field of Classification Search
USPC .......... 602/5, 20, 23; 128/846, 869, 870, 878, 128/881, 882; 160/230; 40/124.01–124.191
See application file for complete search history.

(56) References Cited

U.S. PATENT DOCUMENTS

| | | | |
|---|---|---|---|
| 1,916,789 A | 7/1933 | Fordham | |
| 3,943,923 A | 3/1976 | Scheinberg | |
| 4,209,011 A | 6/1980 | Peck et al. | |
| 4,276,875 A | 7/1981 | Sandegard | |
| 4,580,555 A | 4/1986 | Coppess | |
| 5,591,121 A * | 1/1997 | Cantrell | 602/5 |
| 5,609,567 A | 3/1997 | Kennedy et al. | |
| 5,618,263 A * | 4/1997 | Alivizatos | 602/6 |
| 6,669,659 B2 | 12/2003 | Dittmer et al. | |
| 2008/0249445 A1 * | 10/2008 | Bailey | 602/6 |

* cited by examiner

*Primary Examiner* — Patricia Bianco
*Assistant Examiner* — Keri J Nelson
(74) *Attorney, Agent, or Firm* — Louis Ventre, Jr.

(57) ABSTRACT

A modular articulating splint includes flat slats; a covering that surrounds the slats and holds them in a fixed position spaced apart from each other so that adjacent slats can fold over atop one another to form a stacked deck of slats for storage; and a fabric hook-and-loop fastener for each slat so that the hook portion is affixed to the covering within the width of each slat on a first side and the loop portion is affixed to the covering within the width of each slat on the opposite side.

2 Claims, 1 Drawing Sheet

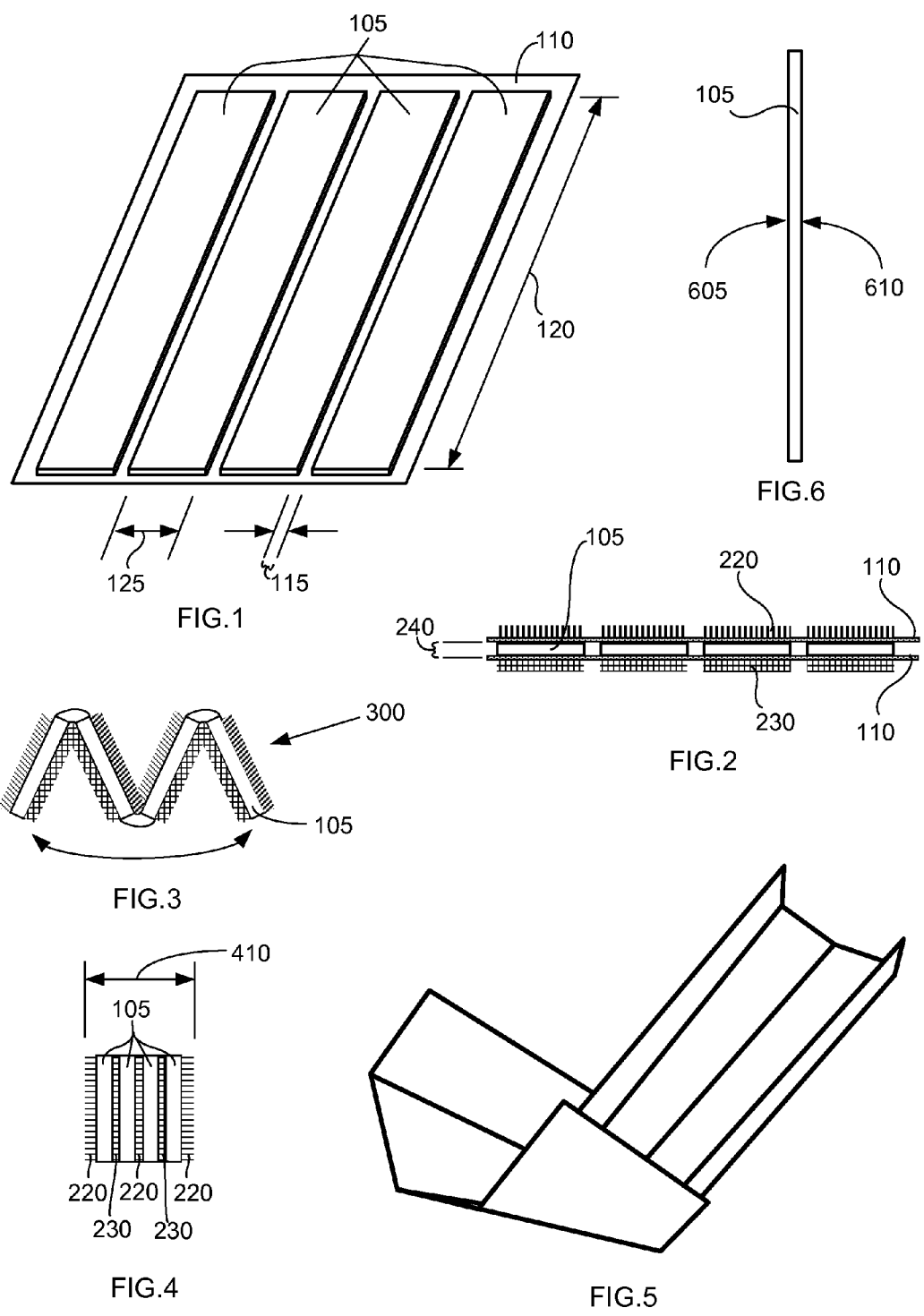

MODULAR ARTICULATING SPLINT

TECHNICAL FIELD

In the field of surgery, an immobilization appliance or splint tends to urge a bandaged body portion into a natural or normal orientation and having a changeable configuration to accommodate the particular requirements.

BACKGROUND ART

Splints are often needed in remote locations to address broken bones or to immobilize a human appendage, such as a broken leg or arm. In civilian life, accident locations such as at a mountain climbing site, a ski slope, or on a remote wilderness trail can present logistical difficulty in attending to a person and immobilizing an injured arm or leg. Emergency medical personnel at the scene of an accident often have need for a fast and efficient means for immobilizing a body part. Military battle field injuries often require quick and effective immobilization often at other than straight configurations, for example arm injuries where holding the arm with a 90 degree angle is preferred.

Portable splints using available technology typically involve a rolled product, such as aluminum covered with a sponge-like material. For remote applications, splints are typically carried, usually in a backpack. Rolled products, while lightweight, are often bulky and time consuming to configure. Existing products are uncoiled or unrolled and then cut to length. In use, such product is usually curved, not flat, so as to provide added resistance to bending stresses when in use.

SUMMARY OF INVENTION

A modular articulating splint includes slats, preferably four flat and thin slats, each about 5 centimeters (2 inches) wide, 31 to 43 centimeters (12 to 17 inches) in length and 2 millimeters (0.08 inches) in thickness. Each slat is flat in that it has two planar faces on opposite sides across the width. A covering, preferably of plastic, vinyl sheeting or other thin lightweight material, surrounds the slats and holds them in a fixed position spaced apart from each other when laid on a flat plane. The distance apart is preferably about 6 millimeters (0.25 inches), but must be of sufficient dimension so that adjacent slats can fold over atop one another to form a stacked deck of slats for storage. A fabric hook-and-loop fastener for each slat in the splint is added so that the hook portion is affixed to the covering within the width of each slat on a first side, and the loop portion is affixed to the covering within the width of each slat on the opposite side.

Technical Problem

Portable splints are bulky, take up too much volume, and can take extra time to properly configure to splint an entire leg. In a combat situation, speed is essential. A splint that can be speedily applied can translate to saving lives. Current technology uses splints that are coiled such that they occupy too much space in a back pack, potentially displacing other needed supplies or equipment. Also, metal based splints must be removed before x-ray examination and thus can needlessly create additional patient pain and discomfort.

Solution to Problem

The solution is a lightweight arrangement of slats held together in a unit by plastic or other material. The slats are arranged near each other to permit folding them together in a stack of rectangular cross-section. When unfolded, the unit may be immediately wrapped around an injury and secured in place to immobilize the injury site. The slats are preferably made of flat, thin plastic, wood or other material that enables x-rays to be taken without removal of the splint. Hook and loop material is secured across the width of each side of the slats. Hook and loop material serves to allow air to enter under the unit around an injury and permits daisy chaining units to lengthen the splint or form complex angles. Preferably, there are 4 slats to a unit so that it easily fits within a backpack having a stack height of about 2 centimeters (0.8 inches), a length of about 43 centimeters (17 inches), and a width of about 5 centimeters (2 inches).

Advantageous Effects of Invention

Preferred embodiments provide stable limb immobilization yet are easy to stow away in a back pack pocket since they are less than an inch in thickness and are lightweight. The preferred design will fit within the wide pockets of a military M-9 bag and also add rigidity to the back pack. The hook and loop material keeps plastic or other covering material off the skin and enables air to circulate around the splinted appendage. These also enable chaining of a second or third unit to make a longer splint or a splint formed at an angle to conform to a bent elbow or knee. The hook and loop material enables two splints to be configured at any desired angle.

BRIEF DESCRIPTION OF DRAWINGS

The drawings illustrate preferred embodiments of the method of the invention and the reference numbers in the drawings are used consistently throughout. New reference numbers in FIG. 2 are given the 200 series numbers. Similarly, new reference numbers in each succeeding drawing are given a corresponding series number beginning with the figure number.

FIG. 1 is a perspective of slats laid out on a portion of a covering.

FIG. 2 is an end view of the splint showing the slats, the covering and a hook and loop material affixed to the covering above and below the slats.

FIG. 3 is an end view of a splint being z-folded to a compact state for storage.

FIG. 4 is an end view of a splint in a fully z-folded state.

FIG. 5 is a perspective of two splints configured together at an angle.

FIG. 6 is a side elevation view of a slat.

DESCRIPTION OF EMBODIMENTS

In the following description, reference is made to the accompanying drawings, which form a part hereof and which illustrate several embodiments of the present invention. The drawings and the preferred embodiments of the invention are presented with the understanding that the present invention is susceptible of embodiments in many different forms and, therefore, other embodiments may be utilized and structural, and operational changes may be made, without departing from the scope of the present invention.

A splint (300) is modular articulating unit illustrated in FIG. 3. The splint (300) is composed of slats (105), shown in FIG. 1; a covering (110); and a fabric hook and loop fastener having a hook portion (220) and a loop portion (230).

Each splint (300) has a plurality of slats, preferably four slats, but there may be more or fewer slats. Preferably, each of the slats (105) has a width (125), a length (120) and a thickness (240), shown in FIG. 2. The preferred dimensions of a slat are about 5 centimeters (2 inches) wide, 43 centimeters (17 inches) in length and 2 millimeters (0.08 inches) in thickness. An alternative preferred splint uses slats (105) with a length (120) of about 31 centimeters (12 inches). The slats (105) are preferably made of lightweight plastic. FIG. 6 shows a preferred slat having at least two planar faces across the width (125), indicated by first arrow (605) and second arrow (610), which are pointing to opposite sides of the slat.

The covering (110) surrounds the slats (105) such that when each of the slats (105) is laid on a planar surface, as shown in FIG. 1, near each other, the covering (110) holds each of the slats (105) in a fixed position with respect to each other. The covering (110) is preferably of plastic sheeting, vinyl sheeting or other thin lightweight material, such as nylon. FIG. 1 shows only half of the covering (110). The covering (110) preferably surrounds or encases the slats (105). Each of the slats (105) is separated from an adjacent slat by a distance (115). The distance (115) is of sufficient dimension so that adjacent slats can fold, preferably in a z-fold as shown in FIG. 3, over atop one another to form a stacked deck of slats, as shown sideways in FIG. 4.

A preferred fabric hook-and-loop fastener is presently available under the trade name VELCRO and comes in two pieces, a hook portion (220) and a loop portion (230). Hook-and-loop fasteners are well known to consist of two pieces: typically, two lineal fabric strips which are attached (e.g., stitched or adhered) to the opposing surfaces to be fastened. The first piece is a hook portion (220), which features tiny hooks; the second piece is a loop portion (230) that features even smaller loops. When the two components are pressed together, the hooks catch in the loops and the two pieces fasten or bind temporarily. When the two pieces are separated from each other by pulling or peeling them apart, the fastener remains reusable.

There is one fabric hook-and-loop fastener for each of the slats (105). It consists of a hook portion (220) and a loop portion (230). In the splint (300), one hook portion (220) is affixed to the covering (110) within the width (125) of each slat on a first side of the opposite sides. Similarly, in the splint (300), one loop portion (230) is affixed to the covering (110) within the width (125) of each slat on a second side of the opposite sides. Preferably the hook portion (220) and a loop portion (230) are sewn to the covering (110) so that it mechanically strong connection even in very hot environments.

Preferably, there are 4 slats to a unit so that it easily fits within a backpack having a stack height of about 2 centimeters (0.8 inches), a length of about 43 centimeters (17 inches), and a width of about 5 centimeters (2 inches). An alternative preferred splint uses slats (105) with a length (120) of about 31 centimeters (12 inches). Each slat is preferably about 2 millimeters (0.08 inches) in thickness. With these dimensions, each of the slats (105) has a length-to-width ratio within a range of 12 to 2 and 17 to 2 or about 6 to 8, a width-to-thickness ratio of 2 to 0.08 or 25; and a width-to-distance ratio of 2 to 0.25 or 8. Using these dimensions, the height (410) of a stacked deck of slats is about 2 centimeters (0.8 inches) or about 40% of the width. Since actual dimensions may vary, these preferred dimensions may be phrased as approximate ratios as follows: a length-to-width ratio in a range of about 6 to 8; a width-to-thickness ratio of at least 25; and a width-to-distance ratio of about 8; such that the stacked deck of slats is about 40% of the width.

FIG. 5 is a perspective of two splints configured together at an approximate 90 degree angle, as might be used to conform to a person's arm where splinting across the elbow is necessary. Two or more splints may be connected together in a straight line for longitudinal support to immobilize a leg along its full length. Preferably, when two splints are used, it is best to overlap the splints at least 5 centimeters (2 inches) and this amount is sufficient to make the hook and loop connection sufficiently sturdy to serve to hold together the two splints.

The above-described embodiments including the drawings are examples of the invention and merely provide illustrations of the invention. Other embodiments will be obvious to those skilled in the art. Thus, the scope of the invention is determined by the appended claims and their legal equivalents rather than by the examples given.

INDUSTRIAL APPLICABILITY

The invention has application to the medical and rescue industries.

What is claimed is:
1. A modular articulating splint comprising:
a plurality of slats, wherein each slat in the plurality of slats comprises:
a width; and
two planar faces on opposite sides across the width;
a covering surrounding the plurality of slats, wherein when each of the plurality of slats is laid on a planar surface near each other, said covering holds each of the slats in a fixed position with respect to each other and each slat is separated from an adjacent slat by a distance, said distance being of sufficient dimension so that adjacent slats can fold over atop one another to form a stacked deck of slats;
a fabric hook-and-loop fastener for each slat, wherein each said fabric hook-and-loop fastener comprises a hook portion and a loop portion, wherein one hook portion is affixed to the covering within the width of each slat on a first side of the opposite sides; wherein one loop portion is affixed to the covering within the width of each slat on a second side of the opposite sides.
2. The modular articulating splint of claim 1, wherein the plurality of slats consists of four slats; wherein each slat in the plurality of slats comprises:
a length and a thickness;
a length-to-width ratio in a range of about 6 to 8;
a width-to-thickness ratio of at least 25; and
a width-to-distance ratio of about 8;
such that the stacked deck of slats is about 40% of the width.

* * * * *